United States Patent [19]

Davey

[11] Patent Number: 4,596,872
[45] Date of Patent: Jun. 24, 1986

[54] IMIDAZO[1,2-A]PYRIDINES, AND PROCESS FOR THEIR PREPARATION

[75] Inventor: David D. Davey, Succasunna, N.J.

[73] Assignee: Schering A.G., Berlin, Fed. Rep. of Germany

[21] Appl. No.: 741,427

[22] Filed: Jun. 5, 1985

[51] Int. Cl.$^4$ .................................. C07D 471/02
[52] U.S. Cl. ................................................ 546/121
[58] Field of Search ...................................... 546/121

[56] References Cited

FOREIGN PATENT DOCUMENTS 0068378 1/1983 European Pat. Off. ............ 546/121
0092458 10/1983 European Pat. Off. ............ 546/121

*Primary Examiner*—Henry R. Jiles
*Assistant Examiner*—J. Richter
*Attorney, Agent, or Firm*—Elizabeth A. Bellamy; John L. White; I. William Millen

[57] ABSTRACT

This invention relates to novel substituted imidazo[1,2-a]pyridines, most especially novel 8-phenylimidazo[1,2-a]pyridines and a process for their preparation. The compounds of the invention have been found to have cardiotonic antiarrhythmic, CNS stimulant, CNS depressant and other pharmacological effects.

31 Claims, No Drawings

IMIDAZO[1,2-A]PYRIDINES, AND PROCESS FOR THEIR PREPARATION

FIELD OF INVENTION

This invention relates to novel imidazo[1,2-a]pyridines. More especially this invention relates to novel, variously substituted 8-phenylimidazo[1,2-a]pyridines and their pharmaceutically acceptable acid addition and base addition salts. Further encompassed by the invention is a novel process for the production of the 8-phenyl-imidazo[1,2-a]pyridines as well as their 8-pyridyl-imidazo[1,2-a]pyridine counterparts. The compounds of the invention exhibit a variety of pharmacological properties for which pharmaceutical compositions are proposed.

GENERAL DESCRIPTION OF THE INVENTION

COMPOSITION-OF-MATTER ASPECT

In its composition-of-matter aspect, this invention relates to novel imidazo[1,2-a]pyridines. Particularly, this invention relates to novel, variously substituted 8-phenylimidazo[1,2-a]pyridines and their pharmaceutically acceptable acid addition and base addition salts. Compounds encompassed by the invention are of the following Formula I:

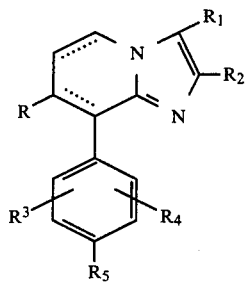

wherein
  R and $R_2$ are hydrogen or lower alkyl;
  $R_1$ is hydrogen, halogen, nitro or amino, $R_3$ and $R_4$ are the same or independently hydrogen, halogen, hydroxy, nitro, amino, lower alkyl, lower alkoxy, lower alkanoylamino or lower alkylsulfonylamino;
  $R_5$ is hydrogen, hydroxy, halogen, nitro, amino, lower alkyl, lower alkoxy, lower alkanoylamino, lower alkylsulfonylamino or 1-imidazolyl optionally substituted by 1 or more lower alkyl groups;
and wherein the dotted lines shall mean the imidazo[1,2-a]pyridine is in the 5,6,7,8-tetrahydro, 5,6-dihydro or fully aromatic form.

As used herein the term "halogen" shall mean fluorine, chlorine or bromine. The term "lower" when used conjunctively with the terms alkyl, alkoxy or alkan shall represent a straight or branched chain alkyl of one to four carbon atoms as for example, methyl, ethyl, propyl, isopropyl, butyl, sec-butyl, isobutyl and tertiary butyl.

Also contemplated as part of this invention are the pharmaceutically acceptable acid addition and base addition salts of the compounds of Formula I. The acid addition salts may be formed with inorganic or organic acids. Illustrative but not restrictive examples of such acids include hydrochloric, hydrobromic, sulfuric, phosphoric, citric, methanesulfonic, 2-hydroxyethane-sulfonic, toluenesulfonic, benzenesulfonic, camphorsulfonic and ethanesulfonic acid. The base addition salts may be formed with the metal ions sodium, potassium or calcium.

It is to be understood that the definition of the compounds of Formula I encompasses all possible stereoisomers and mixtures thereof, which possess the activities discussed below. In particular, it encompasses the geometrical and optical isomers and the racemic modifications thereof which possess the indicated activity.

As stated previously, the compounds of the invention have been found to exhibit a variety of cardiovascular and CNS activities. More particularly, various species have been shown to have cardiotonic, antiarrhythmic, CNS stimulant and CNS depressant activities.

Preferred classes of compounds exhibiting CNS stimulant or depressant activities are those characterized by one or more of the following attributes of the above Formula I. Such compounds are those wherein R is hydrogen or methyl, $R_1$ is hydrogen, halogen, or amino; $R_2$ is hydrogen; $R_3$ and $R_4$ are hydrogen, halogen, lower alkyl or lower alkoxy; $R_5$ is hydrogen, halogen, lower alkyl, lower alkoxy or 1-imidazolyl optionally substituted by one or more lower alkyl groups and where the imidazo[1,2-a]pyridine is in the fully aromatic form.

Preferred compounds of general Formula I which possess cardiotonic and antiarrhythmic properties are those wherein R is hydrogen or methyl; $R_1$, $R_2$, $R_3$ and $R_4$ are hydrogen; $R_5$ is hydrogen, lower alkylsulfonylamino or 1-imidazolyl optionally substituted by one ore more lower alkyl groups and the imidazo[1,2-a]pyridine is in the 5,6-dihydro or fully aromatic form.

The preferred compounds which possess cardiotonic activity are those where R is hydrogen or methyl; $R_1$, $R_2$, $R_3$ and $R_4$ are hydrogen; $R_5$ is hydroxy, methylsulfonylamino or 1-imidazolyl, and the imidazo[1,2-a]pyridine is in the 5,6,7,8,-tetrahydro, 5,6-dihydro or fully aromatic form, with the proviso that when $R_5$ is methylsulfonylamino or 1-imidazolyl the imidazo[1,2-a]pyridine is in the 5,6,7,8,-tetrahydro form.

The preferred compounds which possess antiarrhythmic activity are those where R is hydrogen; $R_1$ is hydrogen or halogen; $R_2$, $R_3$ and $R_4$ are hydrogen; $R_5$ is hydrogen or lower alkyl and the imidazo[1,2-a]pyridine is in the 5,6-dihydro or fully aromatic form.

The following compounds are some of those which serve to exemplify the various composition-of-matter and/or process aspects of the invention as described herein.

(1) 8-(4-chlorophenyl)-5,6-dihydroimidazo[1,2-a]pyridine.
(2) 8-(4-chlorophenyl)imidazo[1,2-a]pyridine.
(3) 5,6-dihydro-8-phenylimidazo[1,2-a]pyridine.
(4) 8-phenylimidazo[1,2-a]pyridine.
(5) 8-(4-hydroxyphenyl)imidazo[1,2-a]pyridine.
(6) 8-(4-hydroxyphenyl)-5,6,7,8-tetrahydroimidazo[1,2-a]pyridine.
(7) 8-[4-(acetamino)phenyl]5,6-dihyroimidazo[1,2-a]pyridine.
(8) 8-(4-aminophenyl)-5,6-dihyroimidazo[1,2-a]pyridine.
(9) 8-(3-amino-4-chlorophenyl)-5,6-dihydroimidazo[1,2-a]pyridine.
(10) 5,6-dihydro-8-(3-methoxyphenyl)imidazo[1,2-a]pyridine.
(11) 5,6-dihydro-8-(3-hydroxphenyl)imidazo[1,2-a]pyridine.
(12) 5,6-dihydro-8-[4-(1H-imidazol-1-yl)phenyl]imidazo[1,2-a]pyridine.

(13) 8-[4-1H-imidazol-1-yl)phenyl]imidazo[1,2-a]pyridine.
(14) 8-[4-(1H-imidazol-1-yl)phenyl]-3-nitroimidazo[1,2-a]pyridine.
(15) 8-[4-(1H-imidazol-1-yl)phenyl]imidazo[1,2-a]pyridine-3-amine.
(16) 3-bromo-8-phenylimidazo[1,2-a]pyridine.
(17) 3-nitro-8-(4-nitrophenyl)imidazo[1,2-a]pyridine.
(18) 8-(4-nitrophenyl)imidazo[1,2-a]pyridine.
(19) 8-(4-aminophenyl)imidazo[1,2-a]pyridine.
(20) 8-[4-((methylsulfonyl)amino)phenyl]imidazo[1,2-a]pyridine.
(21) 5,6-dihydro-8-(4-methylphenyl)imidazo[1,2-a]pyridine.
(22) 8-(4-methylphenyl)imidazo[1,2-a]pyridine.
(23) 8-(4-chlorophenyl)-3-nitroimidazo[1,2-a]pyridine.
(24) 8-(4-chlorophenyl)imidazo[1,2-a]pyridine-3-amine.
(25) 8-[4-(1H-imidazol-1-yl)phenyl]-7-methylimidazo[1.2-a]pyridine.
(26) 4-(imidazo[1,2-a]pyridine-8-yl)benzoic acid.

PROCESS ASPECTS

The major standard synthetic route for the preparation of imidazo[1,2-a]pyridines is based on the condensation of a 2-aminopyridine with an appropriate α-haloketone. The preparation of 8-arylimidazo[1,2-a]pyridines via this route is not practical since the corresponding substituted 2-amino-3-arylpyridines are not readily available. Even the simple parent compound 2-amino-3-phenylpyridine, has not been reported in the literature.

This invention provides a novel synthesis for 8 aryl imidazo[1,2-a]pyridines which is inclusive of the particular 8-phenylimidazo[1,2-a]pyridines of this invention. Essentially, an imidazole is reacted with an arylcyclopropyl ketone or a 4-halobutyroarylone to produce in one step, an 8-aryl-5,6-dihydroimidazo[1,2-a]pyridine.

This novel synthesis is advantageous in that commercially available or readily prepared starting materials are used to prepare the 8-arylimidazo[1,2-a]pyridines. Such starting materials as, for example, the γ-chlorobutyrophenones can be prepared by Friedel Crafts acylation using the corresponding γ-chlorobutyryl chloride. Reaction conditions have to be chosen carefully in order to avoid Friedel-Crafts alkylation, tetralone formation and other side reactions.

Scheme A which follows is illustrative of the synthesis.

Scheme A

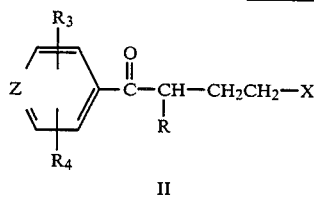

II or

-continued
Scheme A

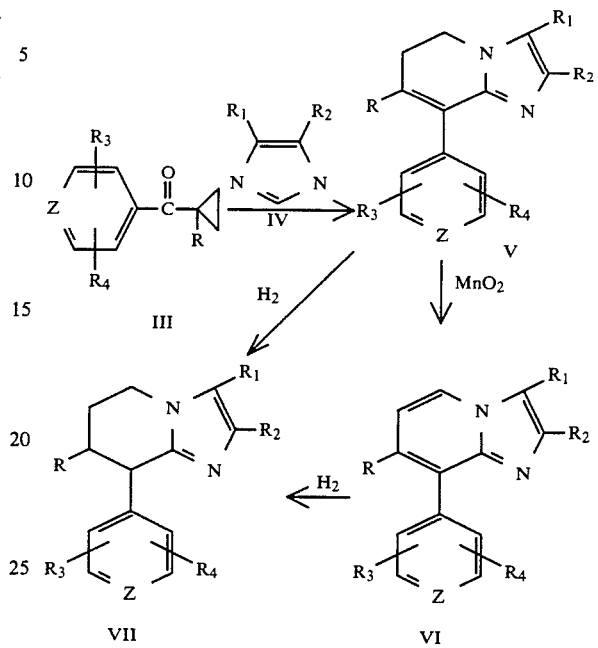

In the foregoing Scheme A, the moieties R, $R_1$, $R_2$, $R_3$ and $R_4$ are as previously defined; X is chlorine or bromine and Z is N or C—$R_5$ where $R_5$ is as previously defined.

The process of Scheme A is carried out by heating one equivalent of a compound of Formula II or III, neat or in an inert solvent with three to ten equivalents of a compound of Formula IV at a temperature of from about 100° to about 250° C., with or without a catalytic amount of an inorganic acid for about 12–48 hours. In the foregoing process the inert solvent is a high boiling variety as for instance decalin, tetralin, 1,2-dichlorobenzene or trichlorobenzene. The temperature range of the reaction is preferably from about 175° C. to about 225° C. and the inorganic acid is selected from the group; hydrochloric, hydrobromic, hydrofluoric, sulfuric or polyphosphoric acids, preferably polyphosphoric acid.

The thus formed 8-aryl-5,6-dihydroimidazo[1,2-a]pyridines of Formula V are isolated by crystallization or by column chromatography. The compounds of Formula V may then be hydrogenated in the presence of catalysts such as palladium or carbon to the tetrahydro derivatives of Formula VII. The compounds of Formula V may also be dehydrogenated, utilizing manganese dioxide in solvents such as benzene or methylene chloride, to form the fully aromatic compounds of Formula VI. The compounds of Formula VI may also be hydrogenated to the compounds of Formula VII.

Some anomalies have been noted in the reaction Scheme A, these can be controlled but for ease of understanding are listed below:

(a) When the reaction is run at high temperatures that is, at or greater than 225° C. mixtures of the tetrahydro and fully aromatic products are produced, which may then be separated by standard techniques.

(b) If Z is C-F in Formula II or III, when, heated with the imidazole, 1-imidazole will replace the fluorine.

(c) If Z or R₃ or R₄ is —OCH₃ in Formula II or III, mixtures of the —OCH₃ and hydroxyl products will result from the reaction. Here again, standard separation techniques are utilized to obtain the products.

METHOD-OF-USE AND PHARMACEUTICAL COMPOSITION ASPECT

The novel 8-phenylimidazo[1,2-a]pyridines of this invention and their pharmaceutically acceptable acid addition and base addition salts have been found to possess a number of important pharmacological characteristics when applied in a number of forms to mammals. Compounds of the general Formula I have been found to possess significant cardiovascular and CNS activities more specifically, cardiotonic, antiarrhythmic, CNS depressant and CNS stimulant properties.

In some cases multiple effects are manifest in a particular compound, while in other cases one or another of these effects is found in a particular compound.

The compounds were tested for their cardiotonoic activity in the isolated cat papillary muscle screen [J. Wiggins, Circ. Res. 49, 718–725 (1981)] and their action was attributed to their ability to increase contractile force in cardiac muscle with minimal effects on heart rate or blood pressure. The compounds were found to have either a short or long term duration of activity. Those of short term would be useful in the treatment of acute heart failure whilst those of long term activity would be useful not only for this indication but also for the treatment of chronic or congestive heart failure. Illustrative, but not exclusive, of the compounds exhibiting significant cardiotonic activity are: 8-(4-hydroxyphenyl)imidazo[1,2-a]pyridine and 8-(4-hydroxyphenyl)-5,6,7,8-tetrahydroimidazo[1,2-a]pyridine.

The antiarrhythmic activity of the compounds was measured by their ability to prolong the action potential of cardiac tissue. Those compounds demonstrating this prolongation of effect are designated in the Vaughan Williams classification as Class III agents and thus are valuable in the treatment of cardiac arrhythmias especially those of the re-entrant type and particularly those associated with the disease state known as chronic ventricular tachycardia. Illustrative of such types of compounds are: 3-bromo-8-phenylimidazo[1,2-a]pyridine, 5,6-dihydro-8-(4-methylphenyl)imidazo[1,2-a]pyridine and 8-(4-methylphenyl)imidazo[1,2-a]pyridine.

CNS tests were conducted using standard neuropharmacological screens such as measuring barbiturate sleeping time, motor activity, gait, etc. to determine the CNS profile. Compounds such as 8-(4-chlorophenyl)imidazo[1,2-a]pyridine and 8-[4-1H-imidazol-1-yl)phenyl]imidazo[1,2-a]pyridine-3-amine, have been found to exhibit CNS-depressant profiles.

As stated previously, certain of the compounds exhibit multiple effects particularly compounds which exhibit both cardiotonic and antiarrhythmic profiles. Illustrative of each compounds are: 5,6-dihydro-8-[4-(1H-imidazol-1-yl)phenyl]imidazol[1,2-a]-pyridine, 8-[4-1H-(imidazol-1-yl)phenyl]imidazo[1,2-a]pyridine and 8-[4-((methylsulfonyl)amino)phenyl]imidazo[1,2-a]pyridine.

The compounds can be administered orally or parenterally. The dosage and method of administration will be dependent on the age, weight, sex and other characteristics of the subject to be treated and the disease state to be treated. The compounds when administered orally or parenterally will be admixed with pharmaceutically acceptable carriers in accordance with standard pharmaceutical practices taking into account the compound to be administered, its dosage form and the disease state it is to effect.

The invention described hereinabove is illustrated below in the Preparations and Examples which, however, is not to be construed as limiting the invention.

PREPARATIONS

PREPARATIONS I

4-Chloro-1-(4-methylphenyl)butan-1-one

To a solution of 100 g (1.1 mole) of toluene and 146 ml (1.3 mole) of 4-chlorobutyryl chloride in 470 ml of carbon disulfide at 10° C. under $N_2$, is added in portions, 180 g (1.4 mole) of aluminum chloride. Stir 1 hr. at 0° C., then discontinue the stirring and allow the reaction mixture to settle for ½ hr. Decant the top carbon disulfide layer and pour the lower layer into concentrated HCl/ice. Extract with two 600 ml portions of methylene chloride. The combined extracts are washed with 1 L of 10% potassium bicarbonate, dried over sodium sulfate and concentrated in vacuo to provide the title compound.

PREPARATION II

Cyclopropyl 4-pyridinyl ketone

To a suspension of 6.0 g (0.83 mole) of lithium wire in 250 ml of ether under argon, is added a solution of 50 g (0.41 mole) of cyclopropyl bromide in 50 ml of ether. A gentle reflux is maintained throughout the addition. Stir for 15 hr. at room temperature. The reaction mixture is added slowly to a solution of 29 g (0.28 mole) of 4-cyanopyridine in 200 ml of ether at −70° C. and stirred at −70° C. for 1 hr. and then allowed to warm to room temperature. Stir at room temperature for 2 hr. then add 70 ml of saturated ammonium chloride and 150 ml of 6N HCl. Extract the reaction mixture with two 500 ml portions of ether. The aqueous portion is made basic with potassium carbonate and extracted with three 500 ml portions of ethylacetate. The combined extracts are dried over magnesium sulfate and concentrated in vacuo. The residue is distilled under vacuum to provide the title compound—bp 65° C. at 0.03 mm Hg.

PREPARATION III

4-Bromo-1-(4-chloro-3-nitrophenyl)butan-1-one 20 g (88.6 mmol) of 4-chloro-3-nitrophenyl cyclopropyl ketone is added to a solution of 65 m of 32% HBr/acetic acid in 300 ml acetic acid and heated to 80° C. for 5 hr. The reaction mixture is cooled to room temperature and poured nto 1 L of 10% potassium carbonate solution, dried over $MgSO_4$ filtered and treated with charcoal. The solvent is removed in vacuo, and the residue is crystallized from ether to provide the title compound.

NMR (CDCl₃): δ=2.2–2.6(quar,2), 3.1–3.4(t,2), 3.5–3.8(t,2) and 7.6–8.5(m,3)ppm.

PREPARATION IV 1-(3-Acetamino-4-chlorophenyl)-4-bromobutan-1-one 18 g of Preparation III is dissolved in 100 ml acetic anhydride with 0.5 g of 5% platinum on carbon, and placed in a Parr hydrogenator at 30 psi for 18 hr. Removal of the catalyst and solvent provides after crystallization from ether the title compound.

NMR (CDCl$_3$): δ=2.0–2.6(m,6), 3.1–3.4(t,2), 3.5–3.8(t,2), and 7.6–8.4(m,3)ppm.

PREPARATION V

8-(3-Acetamino-4-chlorophenyl)-5,6-dihydroimidazo[1,2-a]pyridine 5 g (15.7 mmol) of the compound of Preparation IV and 15 g (0.22 mol) of imidazole is combined and heated to 175° C. under nitrogen for 18 hr. The crude product is isolated by crystallization from ether.

EXAMPLES

Example 1

8-(4-Chlorophenyl)-5,6-dihydroimidazo[1,2-a]pyridine

Combine 25 g (0.14 mol) of 4-chlorophenyl cyclopropyl ketone with 50 g (0.73 mol) of imidazole, and heat to 175° C. for 18 hr. Isolation of the product by column chromatography using 200 g of silica gel and methylene chloride as solvent followed by crystallization from ether affords the title compound.

NMR (CDCl$_3$): δ=2.7(m,2), 4.15(t,2), 6.2(t,1), 6.92(s,1), 7.15(s,1), and 7.5(m,4)ppm.

EXAMPLE 2

8-(4-Chlorophenyl)imidazol[1,2-a]pyridine

Combine 30 g (0.12 mol) of the product from Example 1 with 150 g of "activated" manganese dioxide in 500 ml of methylene chloride, and heat to reflux for 6 hr. Filter off the solids and remove the solvent in vacuo. The residue is crystallized from ether to provide the title compound.

EXAMPLE 3

5,6-Dihydro-8-phenylimidazo[1,2-a]pyridine

Combine 25 g (0.17 mol) of cyclopropyl phenyl ketone with 50 g (0.73 mol) of imidazole, and heat to 200° C. for 18 hr. Isolation from 200 g of silica gel using methylene chloride, followed by crystallization from ether provides the title compound.

NMR (CDCl$_3$): δ=2.4(m,2), 3.9(t,2), 6.1(t,1), and 6.8–8.3(m,8)ppm.

EXAMPLE 4

8-Phenylimidazo[1,2-a]pyridine

Combine 9 g (46 mmol) of the product from Example 3 with 50 g of "activated" manganese dioxide in 200 ml of methylene chloride, and heat to reflux for 8 hr. Filter off the solids and remove the solvent in vacuo. Crystallize the residue from ether to provide the title compound.

NMR (CDCl$_3$): δ=6.85(t,1), 7.27(d,1), 7.40–7.48(m,3), 7.63(d,1), 7.70(d,1), 7.99(d,2), and 8.10(d,1)ppm.

EXAMPLE 5

8-(4-Hydroxyphenyl)imidazo[1,2-a]pyridine

Combine 25 g (0.14 mol) of cyclopropyl 4-methoxyphenyl ketone with 50 g (0.73 mol) of imidazole, and heat to 200°–225° C. for 24 hr. Isolation from 200 g of silica gel using 2% methanol/methylene chloride followed by crystallization from methanol provides the title compound.

NMR (DMSO): δ=6.9(m,3), 7.4(d,1), 7.6(d,1), 8.0(m,3), and 8.5(d,1)ppm.

EXAMPLE 6

8-(4-Hydroxyphenyl)-5,6,7,8-tetrahydroimidazo[1,2-a]pyridine

In the above preparation of Example 5, the column chromatography affords a second fraction. Crystallization from methanol provides the title compound.

NMR (DMSO): δ=1.8(m,2), 2.1(m,1), 3.4(m,1) 3.9(m,3) and 6.6–7.1(m,6)ppm.

EXAMPLE 7

8-(4-Pyridinyl)imidazo[1,2-a]pyridine

Combine 15 g (0.10 mol) of cyclopropyl 4-pyridinyl ketone with 30 g (0.44 mol) of imidazole and heat to 180°–200° C. for 24 hr. Isolation from 200 g silica gel using 5% methanol/methylene chloride followed by crystallization from ether provides the title compound.

NMR (CDCl$_3$): δ=6.8(t,1), 7.3(m,1), 7.6(m,2) and 8.1(m,1)ppm.

EXAMPLE 8

8-[4-(Acetamino)phenyl]5,6-dihydroimidazo[1,2-a]pyridine

Combine 20 g (80 mmol) of 4-acetamino-4-chlorobutyrophenone with 50 g (0.73 mol) of imidazole and heat to 200° C. for 24 hr. Isolation from 200 g of silica gel using 2% methanol/methylene chloride provides the title compound.

EXAMPLE 9

8-(4-Aminophenyl)-5,6-dihydroimidazo[1,2-a]pyridine 5 g of the crude product from Example 8 is dissolved in 10 ml of methanol and added to a solution of 14 g of potassium hydroxide in 15 ml of methanol and 10 ml water. Heat to reflux for 2 hr. Cool to room temperature, and pour into 300 ml of water with good mixing. The resulting precipitate is recrystallized from ether to provide the title compound.

NMR (CDCl$_3$): δ=2.4(m,2), 3.6(s,2), 3.9(t,2), 6.0(t,1), and 7.6–7.8(m,6)ppm.

EXAMPLE 10

8-(3-Amino-4-chlorophenyl)-5,6-dihydroimidazo[1,2-a]pyridine

Combine 5 g (15.7 mmol) of 3'-acetamino-4-bromo-4'-chlorobutyrophenone with 15 g (0.22 mol) of imidazole, and heat to 175° C. for 18 hr. Isolate the crude product by crystallization from ether, and add to a solution of 5 g of potassium hydroxide in 20 ml of 1:1 solution of methanol/water. Heat to reflux for 2 hr. Cool to room temperature, and pour the reaction mixture into 100 ml of water with rapid stirring. The resulting precipitate is recrystallized from ether to provide the title compound.

NMR (CDCl$_3$): δ=2.4(m,2), 3.8(t,2), 6.0(t,1), and 6.8–7.4(m,5)ppm.

EXAMPLE 11

5,6-Dihydro-8-(3-methoxyphenyl)imidazo[1,2-a]pyridine

Combine 35 g of crude cyclopropyl 3-methoxyphenyl ketone with 60 g of imidazole, and heat to 200° C. for 18 hr. Dissolve the reaction mixture in 500 ml of methylene chloride, and wash with three 300 ml portions of water to remove the excess imidazole, further wash with two 100 ml portions of 10% sodium hydroxide. Dry the methylene chloride portion over magnesium sulfate, and remove the solvent in vacuo. Crystallize the residue from ether to provide the title compound.

NMR (CDCl$_3$): δ=2.4(m,2), 4.8(s,3), 4.9(t,2), 6.1(t,1), and 6.8–7.1(m,6)ppm.

EXAMPLE 12

5,6-Dihydro-8-(3-hydroxyphenyl)imidazo[1,2-a]pyridine

Combine the sodium hydroxide washes from the preparation of Example 11, and neutralize with solid ammonium chloride. Recrystallize the resulting precipitate from 1:1 methanol/methylene chloride to provide the title compound.

NMR (CF$_3$CO$_2$H): δ=2.8(m,2), 4.3(t,2), and 6.6–7.7(m,7)ppm.

EXAMPLE 13

5,6-Dihydro-8-[4-(1H-imidazol-1-yl)phenyl]imidazo[1,2-a]-pyridine

Combine 50 g (0.25 mol) of 4-chloro-4′-fluorobutyrophenone with 120 g (1.76 mol) of imidazole, and heat to 175° C. for 18 hr. Isolation of the product from 500 g of silica gel, followed by crystallization from ethyl acetate, provides the title compound.

NMR (CDCl$_3$): δ=2.5(m,2), 4.0(t,2), 6.2(t.1), 6.9(d,1), and 7.1–8.0(m,8)ppm.

EXAMPLE 14

8-[4-1H-Imidazol-1-yl)phenyl]imidazo[1,2-a]pyridine

Combine 4 g (15.2 mmol) of the product from Example 13 with 10 g of "activated" manganese dioxide in 200 ml of methylene chloride, and heat to reflux for 24 hr. Filter off the solids, and remove the solvent in vacuo. Crystallize the residue from ether to provide the title compound.

NMR (DMSO): δ=7.03(t,1), 7.16(s,1), 7.56(d,1), 7.66(s,1), 7.82(d,2), 7.84(s,1), 8.07(s,1), 8.34(d,2), 8.35(s,1), and 8.60(d,1) ppm.

EXAMPLE 15

8-[4-(1H-Imidazol-1-yl)phenyl[-3-nitroimidazo[1,2-a]pyridine

Add 24 g (92.2 mmol) of the product from Example 14 to 250 ml of concentrated sulfuric acid at 0° C. Add 6 ml of concentrated nitric acid slowly, maintaining the temperature below 5° C. Stir for 30 minutes at 0° C. and then pour the reaction mixture slowly into 3 L of 15% potassium carbonate solution. Filter the precipitate, and then slurry the solids in 4 L of hot water. Filter the solids, slurry in 1 L of isopropanol, and filter. Wash with 500 ml of ether to provide the title compound.

NMR (DMSO): δ=7.15(s,1), 7.55(m,1), 7.81(m,3), 8.02–8.35(m,3), 8.36(m,1), 8.81(m,1), and 9.35(m,1)ppm.

EXAMPLE 16

8-[4-(1H-Imidazol-1-yl)phenyl]imidazo[1,2-a]pyridine-3-amine

To a slurry of 15 g (49.1 mmol) of the product from Example 15 in 500 ml of acetic acid, add 50 g of iron powder with good mixing. Heat to 60° C. for 1.5 hr. Filter off the solids and remove the solvent in vacuo. Add the residue to 2 L of 10% sodium hydroxide and extract two 1 L portions of methylene chloride. Dry the combined extracts over magnesium sulfate, treat with charcoal, filter, and remove the solvent in vacuo. Crystallize the residue from tetrahydrofuran to provide the title compound.

NMR (DMSO): δ=5.12(s,2), 6.95(m,2), 7.16(s,1), 7.36(d,1), 7.76–7.84(m,3), 8.12(d,1) and 8.36(m,3)ppm.

EXAMPLE 17

3-Bromo-8-phenylimidazo[1,2-a]pyridine

Combine 2 g (10.3 mmol) of the product from Example 4 with 1.8 g (10.3 mmol) of N-bromosuccinimide in 50 ml of methylene chloride, and stir for 10 minutes at room temperature. Wash the reaction mixture with 50 ml of 10% potassium carbonate. Dry the methylene chloride layer over sodium sulfate, treat with charcoal, filter, and remove the solvent in vacuo. Crystallize the residue from ether to provide the title compound.

NMR (CDCl$_3$): δ=7.01(t,1), 7.34–7.50(m,4), 7.69(s,1), 7.94(m,2) and 8.02(m,1)ppm.

EXAMPLE 18

3-Nitro-8-(4-nitrophenyl)imidazo[1,2-a]pyridine

Add 3.5 g (18.0 mmol) of the product from Example 4 to 25 ml of concentrated sulfuric acid at 0° C. Add 2.5 ml of concentrated nitric acid over a 15 minute period, maintaining the temperature between 0° C. and 5° C. Stir at 0° C. for 30 minutes. Pour the reaction mixture onto 500 ml of ice water and neutralize with potassium carbonate. Filter the resulting precipitate and slurry the filter cake in 2 L of hot water. Filter and wash with 2 L of hot water. Slurry the filter cake in 500 ml of isopropanol, filter and wash with 100 ml of isopropanol to provide the title compound.

NMR (DMSO): δ=7.64(t,1), 8.16(d,1), 8.33(d,2), 8.87(s,1) and 9.45(d,1)ppm.

EXAMPLE 19

8-(4-Nitrophenyl)imidazo[1,2-a]pyridine

Add 20 g (0.10 mole) of the product from Example 4 slowly to 150 ml of concentrated sulfuric acid at −15° C. Add 7 ml of concentrated nitric acid slowly, maintaining the temperature −10° C. Stir at −10° C. for 30 minutes. Pour onto 500 g of ice. Add 2 L of water and neutralize with potassium carbonate. Extract with three 500 ml portions of methylene chloride. Combine the extracts, dry over magnesium sulfate, treat with charcoal and remove the solvent in vacuo. The residue is crystallized from ether to provide the title compound.

EXAMPLE 20

8-(4-Aminophenyl)imidazo[1,2-a]pyridine

Add 45 g of iron powder to a solution of 15 g (62.7 mmol) of the product from Example 19 in 400 ml of 75% acetic acid. Heat to 60°–70° C. for 2 hr. Filter the reaction mixture over celite and concentrate the filtrate to approximately 50 ml under vacuum. Neutralize the residue with saturated sodium carbonate solution and extract with three 200 ml portions of methylene chloride. Dry the combined extracts over sodium sulfate, treat with charcoal and remove the solvent in vacuo. Crystallize the residue from ether to provide the title compound.

NMR (CDCl$_3$) δ=3.75(s,2), 6.79(m,3), 7.21(d,1), 7.60(s,1), 7.67(s,1), 7.86(d,2) and 8.04(d,1)ppm.

EXAMPLE 21

8-[4-((Methylsulfonyl)amino)phenyl]imidazo[1,2-a]pyridine

Dissolve 4 g (19.1 mmol) of the product from Example 20, in 100 ml of methylene chloride and cool to 0° C. Add 1.6 ml of methanesulfonyl chloride slowly, maintaining the temperature at 5° C. Stir at r.t. for 12 hr. Extract the reaction mixture with 100 ml of 10% sodium hydroxide. Wash with 100 ml of methylene chloride and with 100 ml of ether. Treat with charcoal and neutralize with ammonium chloride. The resulting precipitate is filtered and washed with water to provide the title compound.

NMR (DMSO): $\delta = 3.06(s,3)$, $6.99(t,1)$, $7.32(d,2)$, $7.43(d,1)$, $7.63(s,1)$, $8.03(s,1)$, $8.03(s,1)$, $8.15(d,2)$, $8.54(d,1)$ and $9.91(s,1)$ ppm.

EXAMPLE 22

5,6-Dihydro-8-(4-methylphenyl)imidazo[1,2-a]pyridine

Combine 100 g (0.51 mole) of 4-chloro-4'-methylbutyrophenone with 300 g (4.4 mole) of imidazole and heat to 175° C. under nitrogen for 24 hr. Purification from 1 kg of silica gel using methylene chloride as solvent, followed by crystallization from ether provides the title compound.

NMR (CDCl₃): $\delta = 2.63(s,3)$, $2.68(m,2)$, $4.11(t,2)$, $6.14(t,1)$, $6.89(s,1)$, $7.09(s,1)$, $7.22(d,1)$ and $7.55(d,1)$ ppm.

EXAMPLE 23

8-(4-Methylphenyl)imidazo[1,2-a]pyridine

Combine 30 g (0.14 mole) of the product from Example 22 with 150 g of "activated" manganese dioxide in 500 ml of methylene chloride and heat to reflux for 6 hr. Filter the reaction mixture over celite, dry over magnesium sulfate, treat with charcoal, and remove the solvent in vacuo. Crystallize the residue from ether to provide the title compound.

NMR (CDCl₃): $\delta = 2.41(s,3)$, $6.83(t,1)$, $7.27(d,1)$, $7.30(d,1)$, $7.62(s,1)$, $7.68(s,1)$, $7.89(d,1)$ and $8.08(d,1)$ ppm.

Contemplated as equivalents to the compounds of this invention are those of the following Formula VIII.

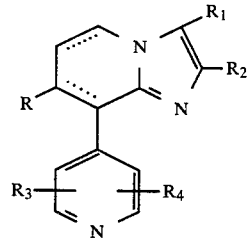

VIII wherein R, $R_1$, $R_2$, $R_3$ and $R_4$ and the pharmaceutically acceptable salts take the same meaning as in Formula I.

Formula VIII compounds are exemplified by, for example, 8-(4-pyridinyl)imidazo[1,2-a]pyridine and others.

I claim:

1. A compound of the Formula I

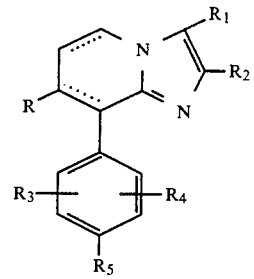

wherein

R and $R_2$ are hydrogen or lower alkyl;

$R_1$ is hydrogen, halogen, nitro or amino;

$R_3$ and $R_4$ are the same or independently hydrogen, halogen, hydroxy, nitro, amino, lower alkyl, lower alkoxy, lower alkanoylamino, lower alkylsulfonylamino;

$R_5$ is hydrogen, hydroxy, halogen, nitro, amino, lower alkyl, lower alkoxy, lower alkanoylamino, alkylsulfonylamino, or 1-imidazolyl optionally substituted by one or more lower alkyl groups;

and wherein the dotted lines shall mean the imidazo[1,2-a]pyridine is in the 5,6,7,8-tetrahydro, 5,6-dihydro or fully aromatic form; and the pharmaceutically acceptable acid addition or base addition salts thereof.

2. A compound of claim 1 wherein R is hydrogen or methyl; $R_1$ is hydrogen, halogen or amino; $R_2$ is hydrogen; $R_3$ and $R_4$ are hydrogen, halogen, lower alkyl or lower alkoxy; $R_5$ is hydrogen, halogen, lower alkyl, lower alkoxy or 1-imidazolyl optionally substituted by one or more lower alkyl groups; and the imidazo[1,2,-a]pyridine is in the fully aromatic form.

3. A compound of claim 1 wherein R is hydrogen or methyl; $R_1$, $R_2$, $R_3$ and $R_4$ are hydrogen; $R_5$ is hydrogen, lower alkylsulfonylamino or 1-imidazolyl optionally substituted by one or more lower alkyl groups and the imidazo[1,2-a]pyridine is in the 5,6-dihydro or fully aromatic form.

4. A compound of claim 1 wherein R is hydrogen or methyl; $R_1$, $R_2$, $R_3$ and $R_4$ are hydrogen; $R_5$ is hydroxy, methylsulfonylamino or 1-imidazolyl and the imidazo[1,2-a]pyridine is in the 5,6,7,8-tetrahydro, 5,6-dihydro or fully aromatic form; with the proviso that when $R_5$ is methylsulfonylamino or 1-imidazolyl the imidazo[1,2-a]pyridine is in the 5,6,7,8-tetrahydro form.

5. A compound of claim 1 wherein $R_1$, $R_2$, $R_3$ and $R_4$ are hydrogen; $R_1$ is hydrogen or halogen; $R_5$ is hydrogen or lower alkyl and the imidazo[1,2-a]pyridine is in the 5,6-dihydro or fully aromatic form.

6. A compound of claim 1 which is 8-(4-chlorophenyl)-5,6-dihydroimidazo[1,2-a]pyridine.

7. A compound of claim 2 which is 8-(4-chlorophenyl)imidazo[1,2-a]pyridine.

8. A compound of claim 1 which is 8-[4-(acetamino)phenyl]-5,6-dihydroimidazo[1,2-a]pyridine.

9. A compound of claim 1 which is 8-(4-aminophenyl)-5,6-dihydroimidazo[1,2-a]pyridine.

10. A compound of claim 1 which is 8-(3-amino-4-chlorophenyl)-5,6-dihydroimidazo[1,2-a]pyridine.

11. A compound of claim 1 which is 5,6-dihydro-8-(3-methoxyphenyl)imidazo[1,2-a]pyridine.

12. A compound of claim 1 which is 5,6-dihydro-8-(3-hydroxyphenyl)imidazo[1,2-a]pyridine.

13. A compound of claim 1 which is 3-nitro-8-(4-nitrophenyl)imidazo[1,2-a]pyridine.

14. A compound of claim 1 which is 8-(4-nitrophenyl)imidazo[1,2-a]pyridine.

15. A compound of claim 1 which is 8-(4-aminophenyl)imidazo[1,2-a]pyridine.

16. A compound of claim 5 which is 5,6-dihydro-8-(4-methylphenyl)imidazo[1,2-a]pyridine.

17. A compound of claim 5 which is 8-(4-methylphenyl)imidazo[1,2-a]pyridine.

18. A compound of claim 1 which is 8-(4-chlorophenyl)-3-nitroimidazo[1,2-a]pyridine.

19. A compound of claim 2 which is 8-(4-chlorophenyl)imidazo[1,2-a]pyridin-3-amine.

20. A compound of claim 1 which is 8-[4-(1H-imidazol-1-yl)phenyl]-3-nitroimidazo[1,2-a]pyridine.

21. A compound of claim 2 which is 8-[4-(1H-imidazol-1-yl)phenyl]imidazo[1,2-a]pyridine-3-amine.

22. A compound of claim 3 which is 8-phenylimidazo[1,2-a]pyridine.

23. A compound of claim 4 which is 8-(4-hydroxyphenyl)-5,6,7,8-tetrahydroimidazo[1,2-a]pyridine.

24. A compound of claim 5 which is 3-bromo-8-phenylimidazo[1,2-a]pyridine.

25. A compound of claim 5 which is 8-(4-hydroxyphenyl)imidazo[1,2-a]pyridine.

26. A compound of claim 3 which is 5,6-dihydro-8-[4-(1H-imidazol-1-yl)phenyl]imidazo[1,2-a]pyridine.

27. A compound of claim 3 which is 8-[4-(1H-imidazol-1-yl)phenyl]imidazo[1,2-a]pyridine.

28. A compound of claim 3 which is 8-[4-(methylsulfonyl)amino)phenyl]imidazo[1,2-a]pyridine.

29. A compound of claim 4 which is 8-[4-(1H-imidazol-1-yl)phenyl]-7-methylimidazo[1,2-a]pyridine.

30. A compound of claim 5 which is 5,6-dihydro-8-phenylimidazo[1,2-a]pyridine.

31. A process for the preparation of an imidazo[1,2-a]pyridine of the Formula II:

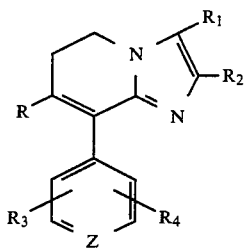

wherein
R and $R_2$ are hydrogen or lower alkyl;
$R_1$ is hydrogen, halogen, nitro or amino;
$R_3$ and $R_4$ are the same or independently hydrogen, halogen, hydroxy, nitro, amino, lower alkyl, lower alkoxy, lower alkanoylamino, lower alkylsulfonylamino;
Z is nitrogen or C-$R_5$;
$R_5$ is hydrogen, hydroxy, halogen, nitro, amino, lower alkyl, lower alkoxy, lower alkanoylamino, lower alkylsulfonylamino or 1-imidazolyl optionally substituted by one or more lower alkyl groups;
which comprises heating neat or in an inert solvent, with or without a catalytic amount of an inorganic acid, a compound of the Formula III or IV

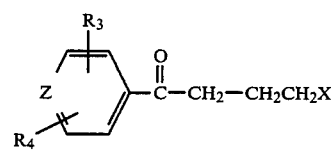

or

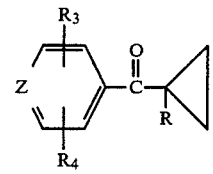

with a 3–10 equivalent excess of an imidazolyl of the Formula V

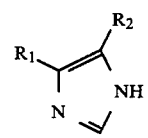

wherein R, $R_1$, $R_2$, $R_3$, $R_4$, $R_5$ and Z have the same meanings as above and where X is chlorine or bromine, at a temperature of from about 100° C. to about 250° C., preferably from about 175° C. to about 225° C. for about 12 to about 48 hours.

* * * * *